United States Patent [19]
Dow et al.

[11] Patent Number: 4,784,148
[45] Date of Patent: Nov. 15, 1988

[54] ULTRASONIC TRANSDUCER PROBE EXPANSION CHAMBER

[75] Inventors: Julian Dow, San Clemente; Paul F. Meyers, San Juan Capistrano, both of Calif.

[73] Assignee: Johnson & Johnson, New Brunswick, N.J.

[21] Appl. No.: 831,787

[22] Filed: Feb. 21, 1986

[51] Int. Cl.⁴ .............................................. A61B 10/00
[52] U.S. Cl. .................................. 128/660.10; 73/633
[58] Field of Search .................. 128/660, 661; 73/627, 73/633, 639

[56] References Cited

U.S. PATENT DOCUMENTS

| | | | |
|---|---|---|---|
| 2,882,503 | 4/1959 | Huff et al. . | |
| 3,175,106 | 3/1965 | Sansom et al. . | |
| 3,800,276 | 3/1974 | Rishell . | |
| 3,854,471 | 12/1974 | Wild . | |
| 3,958,451 | 5/1976 | Richardson . | |
| 3,968,459 | 7/1976 | Jacobson . | |
| 4,059,098 | 11/1977 | Murdock . | |
| 4,074,224 | 2/1978 | Laurent . | |
| 4,103,677 | 8/1978 | Lansiort et al. | 128/660 |
| 4,141,347 | 2/1979 | Green et al. | 730/627 |
| 4,181,120 | 1/1980 | Kunii et al. . | |
| 4,206,763 | 6/1980 | Pedersen | 128/660 |
| 4,217,516 | 8/1980 | Iimima et al. | 128/660 X |
| 4,237,901 | 12/1980 | Taenzer | 128/660 |
| 4,279,167 | 7/1981 | Erb et al. . | |
| 4,316,271 | 2/1982 | Evert | 128/660 |
| 4,391,281 | 7/1983 | Green | 128/660 |
| 4,418,698 | 12/1983 | Dory | 128/660 |
| 4,494,548 | 1/1985 | Buon et al. | 128/661 X |
| 4,517,985 | 5/1985 | Teslawshi et al. | 73/620 X |
| 4,541,436 | 9/1985 | Hassler et al. | 128/660 |

FOREIGN PATENT DOCUMENTS

| | | |
|---|---|---|
| 0089131 | 9/1983 | European Pat. Off. . |

*Primary Examiner*—Francis J. Jaworski
*Attorney, Agent, or Firm*—W. Brinton Yorks, Jr.

[57] ABSTRACT

An ultrasonic transducer probe is provided which utilizes a pivoting transducer to perform an ultrasonic sector scan. The transducer and its drive mechanisms are contained within a fluid chamber. A portion of the wall of the fluid chamber includes a flexible bellows, which expands and contracts as pressure and temperature changes alter the fluid volume, thereby altering the fluid chamber volume.

11 Claims, 2 Drawing Sheets

ULTRASONIC TRANSDUCER PROBE EXPANSION CHAMBER

Figure 1:
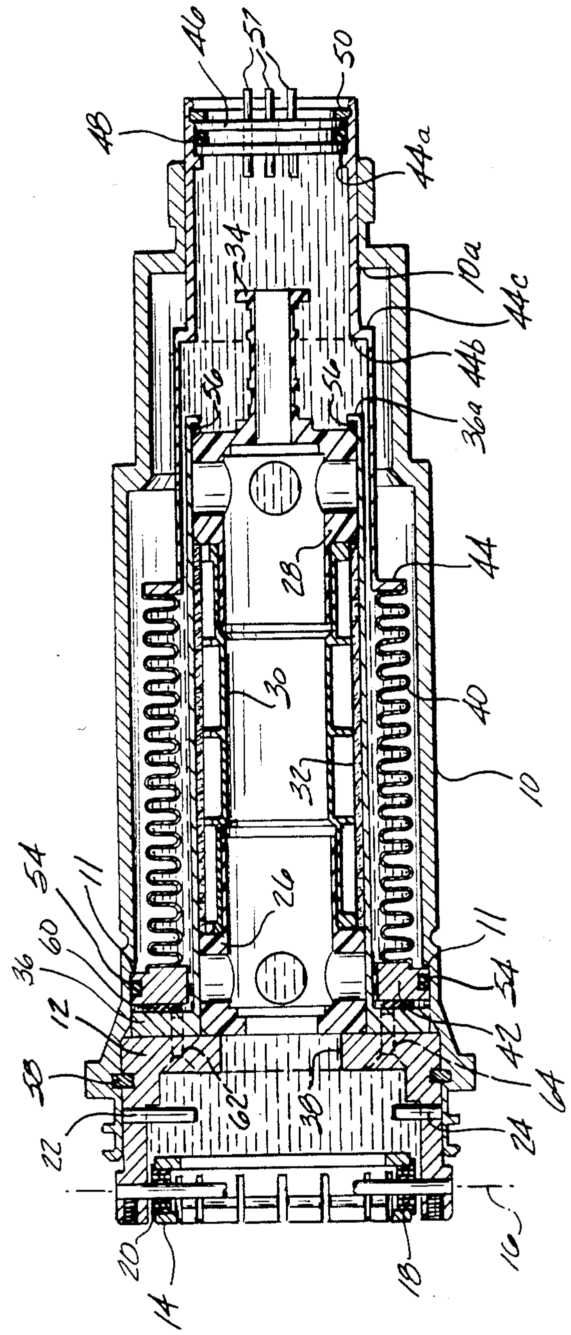

This invention relates to fluid-filled ultrasonic transducer probes for use in ultrasonic diagnostic imaging and, in particular, to expansion chambers for such probes which allow for the expansion coefficient of the fluid as it is affected by temperature changes.

Transducer probes for medical ultrasonic imaging are designed to be small, light, and easy to manipulate for the production of real-time images of the internal tissue structure of a patient. In order to produce real-time images, beams of ultrasonic energy must be rapidly transmitted into the patient and echoes received by the probe for rapid processing into an imaging format suitable for display. Desirably, the probe should produce an image over a wide field of view, such as the so-called sector scan format. A sector scan image is produced by repeatedly transmitting and receiving ultrasonic energy in a number of radial directions from the probe. The ultrasonic beam may be directed either electronically, as by an electronically phased linear transducer array, or it may be directed mechanically by a mechanically moving transducer. The present invention is particularly useful in mechanically moving transducer probes, in which the transducer is physically swept through an arc to produce a sector scan. Such mechanical probes may be advantageous compared with phased array probes when a relatively simple mechanical drive assembly in the mechanical probe is used to perform the function of the relatively complex electronics used to "steer" the beam of a phased array probe.

In a mechanical probe, the ultrasonic transducer may be rotated on a wheel or oscillated back and forth by a gimballed mechanism. In either case, the face of the transducer is swept through an arc directed out the acoustic window of the probe which contacts the patient. Because ultrasonic energy does not travel unattenuated through air, and also because additional attenuation is produced if the velocity impedance of the ultrasonic transducer is not matched to the velocity impedance of human tissue, the transducer must be located in a fluid bath which not only readily conducts ultrasonic energy, but furthermore couples the energy with a desired velocity impedance. Generally, the fluid in the probe is a formulation of oil-based materials.

For these reasons, mechanically oscillating transducer probes are conventionally filled with an ultrasonic fluid. The fluid may be located only in a compartment which contains the ultrasonic transducer itself, such as the arrangement shown in U.S. Pat. No. 4,330,874, in which case a dynamic seal of some sort is needed through which the oscillatory driving mechanism passes. However, since dynamic seals often tend to leak over time, it is desirable to locate both the transducer and the driving mechanism in a single fluid compartment, as shown in U.S. patent application No. 691,320, filed Jan. 14, 1985 and now U.S. Pat. No. 4,649,925. In this latter case, only static, electrical connections must pass into the fluid compartment, which greatly reduces the possibility of fluid leaks.

Fluid leakage is particularly undesirable because, as the fluid leaks out, the lost fluid is replaced by air as the pressure within the probe equalizes to outside atmospheric pressure. Once in the fluid compartment, the air bubbles will soon make their way to the transducer region of the compartment. When the air bubbles are located in front of the face of the ultrasonic transducer they will cause the problems necessitating the fluid to arise again, as the ultrasonic energy is attenuated and scattered by the air bubbles. The air bubbles can thereby render the transducer probe virtually useless for diagnostic imaging.

A particularly troublesome source of fluid leakage and bubble formation is thermal cycling of the probe. As the probe is warmed, the fluid will expand in accordance with its temperature expansion coefficient. The pressure within the fluid compartment will build and some fluid may leak out. When the probe is thereafter cooled, the fluid will contract, which creates a negative pressure in the compartment relative to atmospheric pressure until air leaks in to equalize the pressure. Such thermal cycling may occur, for instance, when a probe is left in the trunk of a car on a warm day, and is then taken into an air-conditioned building.

To account for the effects of thermal cycling, probes may incorporate what are known as expansion chambers. The expansion chamber is a part of the fluid compartment which is flexible. The wall or membrane of the expansion chamber has the fluid of the compartment on one side, and is exposed to atmospheric pressure on the other. As the fluid expands and contracts, the expansion chamber will likewise expand and contract to maintain the desired fluid pressure within the compartment as the fluid volume changes. Desirably, the expansion chamber should be large to accommodate wide variations in the fluid volume. A large expansion chamber will respond to fluid volume changes with relatively little distension of the chamber. However, the desirability of a large expansion chamber runs counter to the favored design characteristics of the probe itself, which are that the probe should be made as small and light as possible.

In accordance with the principles of the present invention, an expansion chamber for an ultrasonic transducer probe is provided which is large enough to accommodate large variations in fluid volume with relatively little distension, while at the same time being arranged to permit a compact probe design. This is accomplished by surrounding a portion of the probe mechanism with the expansion chamber. Unlike prior art expansion chambers, there is no wasted space resulting from the use of a separate volume of the probe solely for the expansion chamber. The volume encompassed by an expansion chamber which houses a portion of the probe mechanism can be made relatively sizeable, providing the benefit of accommodating significant temperature changes without significant percentage change in the volume or overall dimensions of the chamber.

Figure 2:
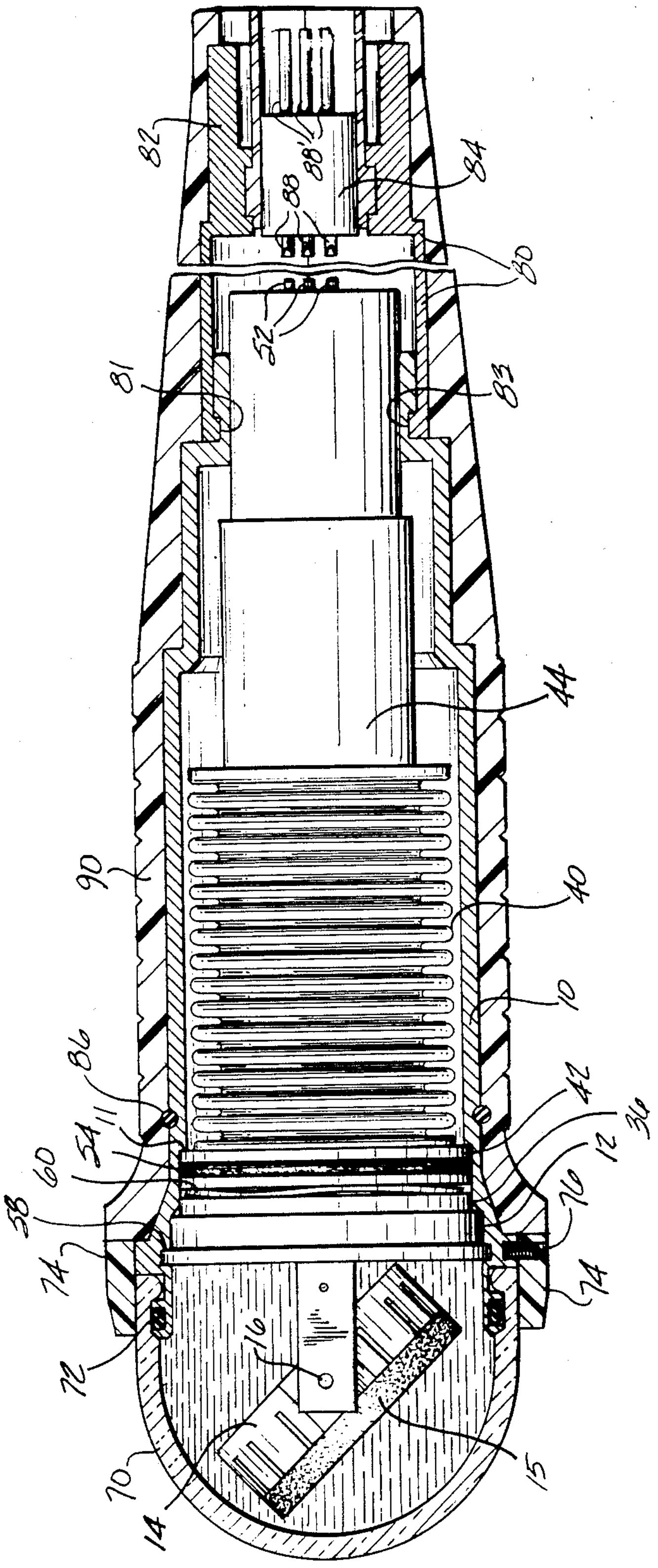

In the drawings:

FIG. 1 is a cross-sectional illustration of an ultrasonic transducer probe constructed in accordance with the principles of the present invention; and FIG. 2 illustrates the probe of FIG. 1 when enclosed in a case and acoustic lens cap.

Referring to FIG. 1, an ultrasonic probe constructed in accordance with the principles of the present invention is shown. The probe components are mounted and secured in an aluminum housing 10. At the top of the probe and shown at the left-hand side of the drawing is a gimbal cup 12. The gimbal cup holds a transducer cup 14 at the very top of the probe. The transducer cup is pivotally mounted on an axle, not shown but indicated by its center line 16, which passes through holes in the gimbal cup and bearings 18 and 20 in the cup. An ultrasonic transducer 15 (shown in FIG. 2) snaps into the transducer cup and is pivoted in the cup about the axle to radiate ultrasonic energy in a fan-shaped pattern into a subject as the cup is rocked. Behind the transducer cup on either side of the gimbal cup, and projecting into the space behind the cup are a brass end stop 22 and a transducer cup grounding pin 24. The end stop acts to restrain the transducer cup in the event of any excessive rocking, and the grounding pin is used to ground the transducer cup to the gimbal cup.

The transducer cup is rocked by a linear motor located below the gimbal cup. The motor includes an upper motor bearing 26, a lower motor bearing 28, and a coil former 30. The coil former is encased in a magnet return tube 32. A moving magnet assembly (not shown) rides inside the bearings and is connected by a crankshaft to the transducer cup. As the magnet assembly moves up and down in the motor it rocks the transducer cup in an arcuate motion. An extension of the lower bearing 28 forms a position sensor coil former 34. The motor is contained in a cylindrical support sleeve 36, with the crankshaft (not shown) protruding through a hole in the upper motor bearing 26 and a hole 38 in the bottom of the gimbal cup.

The foregoing components and their operation are more fully described in our U.S. patent application No. 691,320, now U.S. Pat. No. 4,649,925 and entitled "Ultrasonic Transducer Probe Drive Mechanism with Position Sensor", which is hereby incorporated by reference.

In accordance with the principles of the present invention, a bellows 40 surrounds the motor to form an expansion chamber which contains the motor. The bellows is made of copper or brass, is composed of approximately sixteen undulations, and is about one inch long in a constructed embodiment of the present invention. An upper bellows flange 42 is brazed to one end of the bellows and has a groove for an O-ring machined in its outer circumference. A lower bellows flange 44 is brazed to the lower end of the bellows and exhibits a number of shoulders, the purpose of which will be described below. A glass/metal kovar seal and electrical connector 46 is mounted in the end of the lower flange 44. The seal 46 is surrounded by an O-ring 48 to form a fluid seal at the rear of the expansion chamber. The seal 46 is positioned between a shoulder 44*a* in the flange 44 and a snap ring 50 which snaps into a groove in the rear of the flange 44. The pins 52 in the seal 46 are used to make electrical connections from the interior to the exterior of the fluid-filled chamber of the probe. Wires connected to the pins include those from the transducer, the motor coil and the position sensor.

The probe assembly shown in FIG. 1 is assembled as follows. The bellows with its flanges slides into the housing 10 so that the upper flange 42 is seated against a shoulder 11 machined in the interior circumference of the housing. An O-ring 54 forms a fluid seal between the flange 42 and the housing 10. An O-ring 56 is located in the bottom of the motor support sleeve 36 and the motor is slipped into the sleeve. The O-ring 56 acts to shock-mount the motor in the sleeve and also accounts for any tolerancing in the motor components. The gimbal cup and transducer cup are assembled and the transducer is snapped into the transducer cup. The motor and gimbal assemblies are held together and wires from the transducer are run through the hole 38 of the gimbal cup and through grooves in the bearings and return tube to the rear of the motor. Wires from the coil also run to the rear through these grooves. The motor crankshaft is connected to a crank pin in the transducer cup and a snap ring 58 is located in a groove around the gimbal cup. The gimbal cup is then fastened to the motor by screws located in holes 62 and 64 in the gimbal cup and motor support sleeve. Holes 62 and 64 are actually located a plane orthogonal to that of FIG. 1, and on opposite sides of the base of the gimbal cup. A spring washer 60 is located on the upper flange 42. The snap ring 58 is compressed and the entire motor and gimbal assemblies slide into the housing until the snap ring 58 snaps into place in its groove in the inner circumference of the housing 10.

When assembled in this fashion, the motor is seen to be held in its support sleeve by the gimbal cup 12, which presses against the upper bearing 26 and compresses O-ring 56. The motor and gimbal assemblies are positionally located in the housing 10 with reference to the snap ring 58 and its groove in the housing. The spring washer 60, a three-wave spring washer in a constructed embodiment, forces the motor and gimbal assemblies upward so that the snap ring 58 is pressed against the upward wall (left-most in the drawing) of its housing groove. The spring washer also forces the bellows flange 42 downward against shoulder 11. The spring washer 60 further acts as a shock mount in the probe and accounts for tolerancing in the motor sleeve, flange 42, and gimbal cup.

This assembly technique is more fully described in our U.S. patent application No. 691,319, now U.S. Pat. No. 4,688,576 and entitled "Ultrasonic Transducer Probe Assembly".

When assembled thus far, the wires now protruding from the opening at the bottom of the lower flange 44 are soldered to pins 52 of the seal 46. The seal and O-ring 48 are then pressed into position against should 44*a* and held in place by the snap ring 50. This seals the bottom end of the fluid compartment.

The probe is next filled with ultrasonic fluid by submerging it in fluid. The entire interior volume of the probe must be filled without air bubbles, including the gimbal cup, the inside of the bellows, all spaces inside the motor, and the space between the lower bearing 28 and the seal 46. Fluid may also seep into the space between the housing and the bellows and lower flange 44. This fluid will be drained out the bottom of the housing after the filling process.

While the probe is still submerged, the lens cap 70, shown in FIG. 2, is snapped into place to complete the fluid enclosure. An O-ring 72 is first placed around the housing, then the cap 70 is snapped into place. A window ring 74 slides over the cap to hold it securely in place, and the ring 74 is secured in position by a locking screw 76. The filled probe may now be removed from the fluid and drained.

The probe of the present invention is capable of withstanding tremendous changes in temperature and pressure by virtue of its large expansion chamber. The bellows 40 forms a relatively large portion of the exterior of the fluid compartment. Hence, the entire outer compartment wall formed by the bellows can move as ambient pressures and temperatures change. This allows the probe to be shipped in unheated and unpressurized airplane baggage compartments.

Referring to FIG. 1, the range of movement of the fluid compartment is shown. As the bellows expands and contracts in length, the lower flange 44 slides in and out of the bottom of the housing 10. Limits of travel are set by the end 36*a* of the motor sleeve 36 and shoulder 10*a* of the inner circumference of the housing 10. A shoulder in the lower flange 44 travels between these limits. At one extreme, surface 44*b* of the lower flange shoulder will contact end 36*a* of the sleeve 36. At the other extreme, surface 44*c* of the lower flange shoulder will contact shoulder 10*a* of the housing. A constructed embodiment of the present invention is capable of withstanding temperature extremes ranging from −40° C. to +60° C. without rupturing and without the formation of bubbles in the fluid compartment.

FIG. 2 illustrates the final assembly of the probe of the present invention. Wires are run from pins 52 to pins 88 of a connector insert 84, and are soldered in place. Sufficient slack must be left in the wires to accommodate movement of pins 52 toward and away from the insert 84 as expansion and contraction of the bellows 40 moves the lower flange 44. Two halves 80 and 82 of a clamshell-like rear shell housing are hooked around the rear of the housing 10, as indicated at 81 and 83. The rear shell halves enclose the wiring between pins 52 and 88, and hold the connector insert 84 in place at the bottom of the probe. Additionally, the rear shell halves serve as the outer portion of the connector at the rear exterior of the probe where they surround the pins 88'.

Finally, an O-ring 86 is slipped around the housing 10. This O-ring serves to align the housing with a surrounding plastic case 90. The entire assembly is slipped into the plastic case until the case meets the window ring 74 and the O-ring 86 is properly located between the housing and the case. The completed probe is now ready for final inspection, testing and use.

What is claimed is:

1. An ultrasonic transducer probe comprising:

a forward located assembly including a pivotally mounted ultrasonic transducer;

a motor, located to the rear of and connected to said assembly, for controllably moving the transducer to radiantly transmit ultrasonic energy; and an acoustic couplant fluid chamber, enclosing said motor and assembly and including a cap assembly defining a forward hemispheric fluid compartment containing said transducer at the forward end, a rearward located cylinder defining a rearward fluid compartment and having a sealed rearward end and an open forward terminus, and a flexible, cylindrical bellows in fluid-tight connection between said cap assembly defining said hemispheric fluid compartment and said open forward terminus of said cylinder which defines an intermediate fluid compartment of sufficient cross-sectional area to enclose said motor, said cap assembly, bellows, and cylinder defining a contiguous longitudinal acoustic couplant fluid chamber, wherein said bellows comprises means for restricting volumetric variation of said acoustic couplant fluid chamber in response to thermal expansion and contraction of said fluid to longitudinal volumetric variation of said chamber.

2. The ultrasonic transducer probe of claim 1, wherein said flexible bellows circumferentially surrounds at least a portion of said motor and transducer assembly.

3. The ultrasonic transducer probe of claim 2, wherein said bellows includes a first end fixedly mounted with respect to said transducer assembly, and a second end which is capable of movement with respect to said transducer assembly.

4. The ultrasonic transducer probe of claim 2, wherein said pivotally mounted transducer opposes said cap assembly which is fixedly located with respect to said transducer assembly, and said motor opposes said cylinder, said cylinder being capable of movement with respect to said transducer assembly as said bellows flexes.

5. The ultrasonic transducer probe of claim 4, wherein said flexible bellows includes a first end located near said cap assembly and a second end remotely located from said cap assembly, and further comprising a fluid seal, located at said first end of said flexible bellows, for confining acoustic couplant fluid within said fluid chamber.

6. The ultrasonic transducer probe of claim 1, wherein said cylinder includes an electrical connector, mounted in said rearward end, for making electrical connections between the interior and the exterior of said fluid chamber.

7. The ultrasonic transducer probe of claim 6, further comprising a hollow housing which encloses said flexible bellows and at least a portion of said cylinder, said bellows and cylinder being capable of movement within said housing.

8. The ultrasonic transducer probe of claim 7, further including a fluid seal located between the exterior of said bellows and the interior of said housing.

9. The ultrasonic transducer probe of claim 1, wherein said flexible bellows comprises means for varying the separation between said cap assembly and said cylinder as the bellows flexes.

10. The ultrasonic transducer probe of claim 9, wherein said motor is positioned so as to be surrounded by said bellows.

11. The ultrasonic transducer probe of claim 9, wherein said cap assembly includes an ultrasonic aperture and said end of said cylinder includes an electrical connector.

* * * * *